United States Patent [19]

Gautvik et al.

[11] Patent Number: 5,010,010
[45] Date of Patent: Apr. 23, 1991

[54] PRODUCTION OF HUMAN PARATHYROID HORMONE FROM MICROORGANISMS

[75] Inventors: Kaare M. Gautvik, Oslo; Peter Alestrom, Sollihogda; Tordis B. Oven; Odd S. Gabrielsen, both of Oslo, all of Norway

[73] Assignee: Selmer-Sande, A.S., Norway

[21] Appl. No.: 393,851

[22] Filed: Aug. 14, 1989

Related U.S. Application Data

[63] Continuation of Ser. No. 921,684, Oct. 22, 1986, abandoned.

[51] Int. Cl.$^5$ .................. C12P 21/00; C12P 21/02; C12N 1/20; C12N 5/00
[52] U.S. Cl. .................. 435/252.3; 435/252.33; 435/320.1; 435/254; 435/255; 435/256; 435/172.3; 435/69.4; 435/69.7; 536/27; 935/47; 935/48; 935/28
[58] Field of Search ............... 435/68, 70, 172.3, 254, 435/255, 320, 69.4, 69.7, 69.8, 252.3, 252.33; 935/28, 29, 44, 46, 48, 56, 69, 73; 536/27

[56] References Cited

U.S. PATENT DOCUMENTS

| | | | |
|---|---|---|---|
| 4,237,224 | 12/1980 | Cohen et al. | 435/172.3 |
| 4,264,731 | 4/1981 | Shine | 435/172.3 |
| 4,338,397 | 7/1982 | Gilbert et al. | 435/68 |
| 4,366,246 | 12/1982 | Riggs | 435/68 |
| 4,394,443 | 7/1983 | Weissman et al. | 435/91 |
| 4,425,437 | 1/1984 | Riggs | 435/68 |
| 4,468,464 | 8/1984 | Cohen et al. | 435/172.3 |
| 4,532,207 | 7/1985 | Brewer et al. | 435/68 |
| 4,546,082 | 10/1985 | Kurjan et al. | 435/68 |
| 4,588,684 | 5/1986 | Brake | 435/68 |

FOREIGN PATENT DOCUMENTS

| | | | |
|---|---|---|---|
| 038182 | 10/1981 | European Pat. Off. | 435/68 |
| 123544 | 10/1984 | European Pat. Off. | 435/68 |
| 139076 | 5/1985 | European Pat. Off. | 435/68 |
| 8401173 | 3/1984 | PCT Int'l Appl. | 435/68 |
| 2092596A | 8/1982 | United Kingdom | 435/68 |
| 2094833A | 9/1982 | United Kingdom | 435/68 |

OTHER PUBLICATIONS

Chanj et al., Chem. Abst. vol. 92, No. 175928k, 1980 "Initiation of Protein Synthesis in Bacteria at a Translational Start Coden of Mammalian cDNA Effects of Preparathyroid Nucleotide Sequence".

Gonoza et al., Bio Abst. No. 64386, 1982 "Effect of Bases Contiguous to Aug. on Translation Initiation".

Keutmann et al., "Complete Amino Acid Sequence of Human Parathyroid Hormone," *Biochemistry*, vol. 17, 5723 (1978).

Kronenberg et al., "Cloning and Nucleotide Sequence of DNA Coding for Bovine Preproparathyroid Hormone," *Proc. Nat'l. Acad. Sci.*, vol. 76, 4981 (1979).

Gordon et al., (Abstract) "Molecular Cloning and Structural Analysis of Near Full-Length DNA Complementary to the mRNA Coding for Bovine Parathyroid Hormone," *Fed. Proc.*, 39, 947 (1980).

McDevitt et al., (Abstract) "Isolation of Human Parathyroid Hormone Genes," *Calcified Tissue International*, vol. 31, 74 (1980).

Hendy et al., "Nucleotide Sequence of Cloned cDNAs Encoding Human Preproparathyroid Hormone," *Proc. Nat'l. Acad. Sci. USA*, vol. 78, 7365 (1981).

Kronenberg et al., (Abstract) "Structural Analysis of the Human Parathyroid Hormone Gene," *Calcified Tissue International*, vol. 33, 322 (1981).

(List continued on next page.)

*Primary Examiner*—Robin L. Teskin
*Attorney, Agent, or Firm*—Lerner, David, Littenberg, Krumholz & Mentlik

[57] ABSTRACT

The invention provides recombinant plasmids containing in DNA sequences coding for human preproparathyroid hormone. The invention further provides microorganisms, for example *E. coli*, transformed by these plasmids. Finally, the invention also provides a plasmid for insertion into yeast and a transformed yeast in which the plasmid contains DNA coding for parathyroid hormone. Parathyroid hormone is then secreted by the transformed yeast.

38 Claims, 14 Drawing Sheets

OTHER PUBLICATIONS

Born et al., (Abstract) "Expression of Human Preproparathyroid Hormone in *E. coli* and Yeast," *Calcified Tissue International*, vol. 35, 679 (1983).

Born et al., (Abstract) "Expression and Processing of Human Preproparathyroid Hormone in *Escherichia coli*," *Experientia*, vol. 39, 659 (1983).

Naylor et al., "Human Parathyroid Hormone Gene (PTH) is on Short Arm of Chromosome 11," *Somatic Cell Genetics*, vol. 9, (1983).

Vasicek et al., "Nucleotide Sequence of the Human Parathyroid Hormone Gene," *Proc. Nat'l. Acad. Sci.*, vol. 80, 2127 (1983).

Born et al., (Abstract) "Expression of Human Preproparathyroid Hormone in *E. coli* and Yeast," *Calcified Tissue International*, vol. 36 (Suppl. 2), 287 (1984).

Breyel et al., "Synthesis of Mature Human Parathyroid Hormone in *Escherichia coli*," *Third European Congress on Biotechnology*, vol. III, 363 (1984).

Breyel et al., (Abstract) "Synthesis of Mature Hormone Parathyroid Hormone in *Escherichia coil*," *Calcified Tissue International*, vol. 36 (Suppl. 2) 297 (1984).

Hellerman et al., "Secretion of Human Parathyroid Hormone from Rat Pituitary Cells Infected with a Recombinant Retrovirus Encoding Preproparathyroid Hormone," *Proc. Nat'l. Acad. Sci.*, vol. 81, 5340 (1984).

Hendy, (Abstract) "Cloning of Human Parathyroid Hormone mRNA and Gene," *Calcified Tissue International*, vol. 36, 286 (1984).

Kronenberg et al., "Studies of Parathyroid Hormone Secretion Using Recombinant DNA Technology," *Endocrine Control of Bone and Calcium Metabolism*, 217 (1984).

Sung et al., "Hybrid Gene Synthesis: Its Application to the Assembly of DNA Sequences Encoding the Human Parathyroid Hormones and Analogues," *Biochem. Cell Biol.*, vol. 64, 133 (1986).

FIG. 1

DNA sequence for human preproparathyroid hormone.

```
          10                  30                  50
ATGATHCCNGCNAARGAYATGGCNAARGTNATGATHGTNATGYTNGCNATHTGYTTYYTN 70                  90                 110
ACNAARWSNGAYGGNAARWSNGTNAARAARMGNWSNGTNWSNGARATHCARYTNATGCAY 130                 150                 170
AAYYTNGGNAARCAYYTNAAYWSNATGGARMGNGTNGARTGGYTNMGNAARAARYTNCAR 190                 210                 230
GAYGTNCAYAAYTTYGTNGCNYTNGGNGCNCCNYTNGCNCCNMGNGAYGCNGGNWSNCAR 250                 270                 290
MGNCCNMGNAARAARGARGAYAAYGTNYTNGTNGARWSNCAYGARAARWSNYTNGGNGAR 310                 330
GCNGAYAARGCNGAYGTNAAYGTNYTNACNAARGCNAARWSNCARTRR
```

DNA sequence for human
preproparathyroid hormone in plasmid pSSHPTH-10.

```
         10                  30                  50
ATGATGATACCTGCAAAAGACATGGCTAAAGTTATGATTGTCATGTTGGCAATTTGTTTT 70                  90                 110
CTTACAAAATCGGATGGGAAATCTGTTAAGAAGAGATCTGTGAGTGAAATACAGCTTATG 130                 150                 170
CATAACCTGGGAAAACATCTGAACTCGATGGAGAGAGTAGAATGGCTGCGTAAGAAGCTG 190                 210                 230
CAGGATGTGCACAATTTTGTTGCCCTTGGAGCTCCTCTAGCTCCCAGAGATGCTGGTTCC 250                 270                 290
CAGAGGCCCCGAAAAAAGGAAGACAATGTCTTGGTTGAGAGCCATGAAAAAAGTCTTGGA 310                 330
GAGGCAGACAAAGCTGATGTGAATGTATTAACTAAAGCTAAATCCCAGTGA
```

FIG. 3

Portion of DNA sequence of the plasmid for insertion into E. coli, coding for human preproparathyroid hormone with flanking sequences.

```
        10                  30                  50
TATGATGATHCCNGCNAARGAYATGGCNAARGTNATGATHGTNATGYTNGCNATHTGYTT 70                  90                 110
YYTNACNAARWSNGAYGGNAARWSNGTNAARAARMGNWSNGTNWSNGARATHCARYTNAT 130                 150                 170
GCAYAAYYTNGGNAARCAYYTNAAYWSNATGGARMGNGTNGARTGGYTNMGNAARAARYT 190                 210                 230
NCARGAYGTNCAYAAYTTYGTNGCNYTNGGNGCNCCNYTNGCNCCNMGNGAYGCNGGNWS 250                 270                 290
NCARMGNCCNMGNAARAARGARGAYAAYGTNYTNGTNGARWSNCAYGARAARWSNYTNGG 310                 330                 350
NGARGCNGAYAARGCNGAYGTNAAYGTNYTNACNAARGCNAARWSNCARTRRAAATGAAA 370                 390                 410
ACAGATATTGTCAGAGTTCTGCTCTAGACAGTGTAGGGCAACAATACATGCTGCTAATTC

430
AAAGCTCTATTA
```

DNA sequence for human preproparathyroid hormone in plasmid pSSHPTH-10 with flanking sequences.

```
         10                  30                  50
TATGATGATACCTGCAAAAGACATGGCTAAAGTTATGATTGTCATGTTGGCAATTTGTTT 70                  90                 110
TCTTACAAAATCGGATGGGAAATCTGTTAAGAAGAGATCTGTGAGTGAAATACAGCTTAT 130                 150                 170
GCATAACCTGGGAAAACATCTGAACTCGATGGAGAGAGTAGAATGGCTGCGTAAGAAGCT 190                 210                 230
GCAGGATGTGCACAATTTTGTTGCCCTTGGAGCTCCTCTAGCTCCCAGAGATGCTGGTTC 250                 270                 290
CCAGAGGCCCCGAAAAAAGGAAGACAATGTCTTGGTTGAGAGCCATGAAAAAAGTCTTGG 310                 330                 350
AGAGGCAGACAAAGCTGATGTGAATGTATTAACTAAAGCTAAATCCCAGTGAAAATGAAA 370                 390                 410
ACAGATATTGTCAGAGTTCTGCTCTAGACAGTGTAGGGCAACAATACATGCTGCTAATTC

430
AAAGCTCTATTA.
```

FIG. 5

DNA sequence coding for preproparathyroid hormone in pSSHPTH-10 with flanking sequences, showing the corresponding amino acid sequence of preproparathyroid hormone.

```
         10                  30                  50
TATGATGATACCTGCAAAAGACATGGCTAAAGTTATGATTGTCATGTTGGCAATTTGTTT
   MetIleProAlaLysAspMetAlaLysValMetIleValMetLeuAlaIleCysPh 70                  90                 110
TCTTACAAAATCGGATGGGAAATCTGTTAAGAAGAGATCTGTGAGTGAAATACAGCTTAT
eLeuThrLysSerAspGlyLysSerValLysLysArgSerValSerGluIleGlnLeuMe 130                 150                 170
GCATAACCTGGGAAAACATCTGAACTCGATGGAGAGAGTAGAATGGCTGCGTAAGAAGCT
tHisAsnLeuGlyLysHisLeuAsnSerMetGluArgValGluTrpLeuArgLysLysLe 190                 210                 230
GCAGGATGTGCACAATTTTGTTGCCCTTGGAGCTCCTCTAGCTCCCAGAGATGCTGGTTC
uGlnAspValHisAsnPheValAlaLeuGlyAlaProLeuAlaProArgAspAlaGlySe 250                 270                 290
CCAGAGGCCCCGAAAAAAGGAAGACAATGTCTTGGTTGAGAGCCATGAAAAAAGTCTTGG
rGlnArgProArgLysLysGluAspAsnValLeuValGluSerHisGluLysSerLeuGl 310                 330                 350
AGAGGCAGACAAAGCTGATGTGAATGTATTAACTAAAGCTAAATCCCAGTGAAAATGAAA
yGluAlaAspLysAlaAspValAsnValLeuThrLysAlaLysSerGlnEnd 370                 390                 410
ACAGATATTGTCAGAGTTCTGCTCTAGACAGTGTAGGGCAACAATACATGCTGCTAATTC

430
AAAGCTCTATTA.
```

SCHEMATIC DRAWING OF RECOMBINANT PLASMID pSSHPTH-10

SCHEMATIC DRAWING OF pALX4

CONSTRUCTION OF pαLX5 FROM pMFα1-1 AND pL4

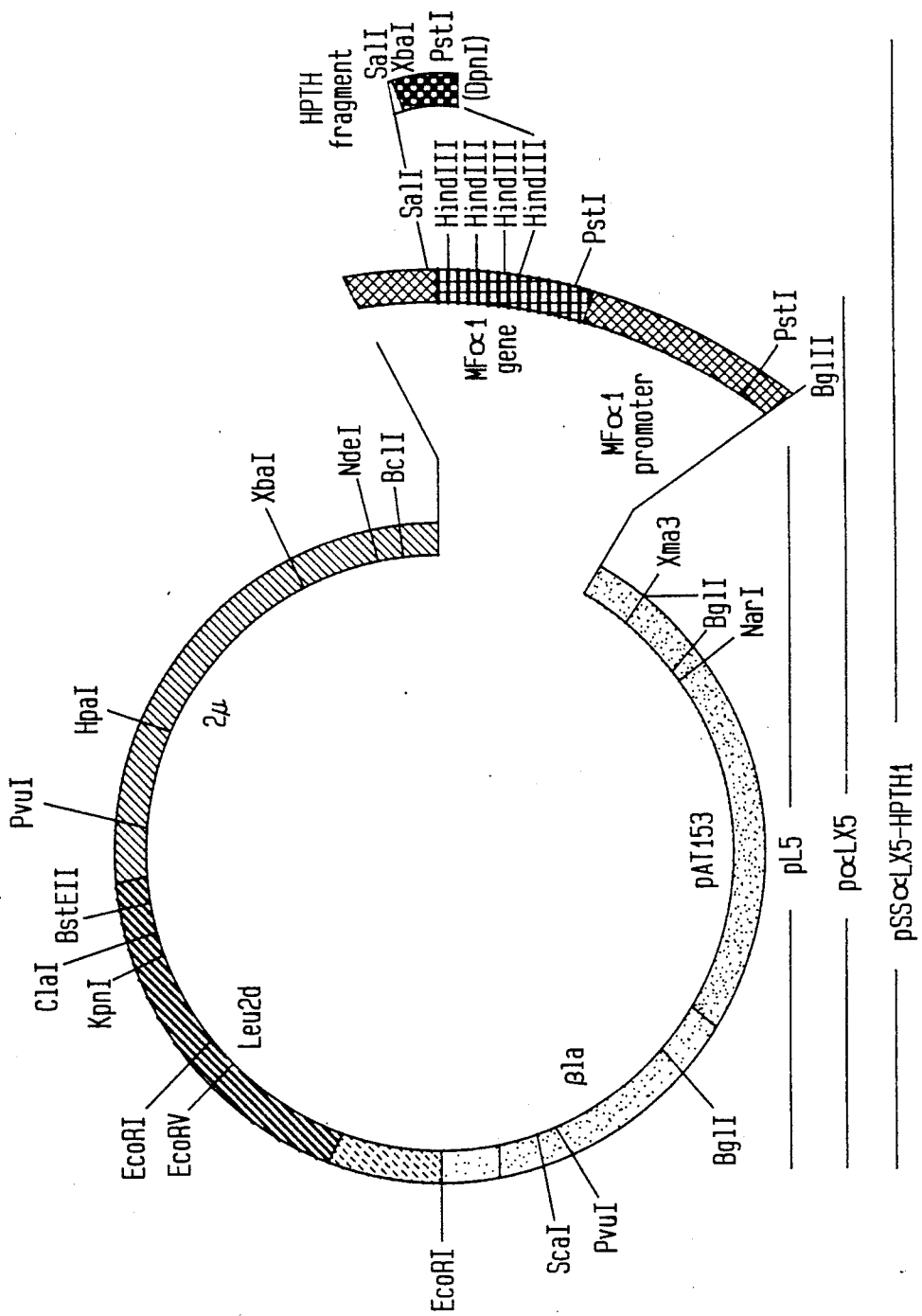
FIG. 9 SCHEMATIC DRAWING OF pSSαLX5-HPTH1, SHOWING THE pL5, SalI DIGESTED pαLX5 AND MFα1 FRAGMENTS

FIG. 10

Partial DNA sequence for the plasmid for insertion into yeast in which: Nucleotide nos. 1-173 makeup the MFα1 promoter region and 5' noncoding sequence. 174-440 is the MFα1 N-terminal coding sequence. 441-695 is an HPTH sequence. 696-726 is an HPTH 3' noncoding sequence from pSSHPTH-10. 727-732 is from pUC19. 733-874 is MFα1 3' noncoding sequence and transcriptional termination signal.

```
            10                  30                  50
AGTGCAAGAAAACCAAAAAGCAACAACAGGTTTTGGATAAGTACATATATAAGAGGGCCT 70                  90                 110
TTTGTTCCCATCAAAAATGTTACTGTTCTTACGATTCATTTACGATTCAAGAATAGTTCA 130                 150                 170
AACAAGAAGATTACAAACTATCAATTTCATACACAATATAAACGACCAAAAGAATGAGAT 190                 210                 230
TTCCTTCAATTTTTACTGCAGTTTTATTCGCAGCATCCTCCGCATTAGCTGCTCCAGTCA 250                 270                 290
ACACTACAACAGAAGATGAAACGGCACAAATTCCGGCTGAAGCTGTCATCGGTTACTCAG 310                 330                 350
ATTTAGAAGGGGATTTCGATGTTGCTGTTTTGCCATTTTCCAACAGCACAAATAACGGGT 370                 390                 410
TATTGTTTATAAATACTACTATTGCCAGCATTGCTGCTAAAGAAGAAGGGGTATCTTTGG 430                 450                 470
ATAAAAGAGAGGCTGAAGCTWSNGTNWSNGARATHCARYTNATGCAYAAYYTNGGNAARC 490                 510                 530
AYYTNAAYWSNATGGARMGNGTNGARTGGYTNMGNAARAARYTNCARGAYGTNCAYAAYT 550                 570                 590
TYGTNGCNYTNGGNGCNCCNYTNGCNCCNMGNGAYGCNGGNWSNCARMGNCCNMGNAARA
```

FIG. 10 CONT.

```
          610                 630                 650
ARGARGAYAAYGTNYTNGTNGARWSNCAYGARAARWSNYTNGGNGARGCNGAYAARGCNG 670                 690                 710
AYGTNAAYGTNYTNACNAARGCNAARWSNCARTRRAAATGAAAACAGATATTGTCAGAGT 730                 750                 770
TCTGCTCTAGAGTCGACTTTGTTCCCACTGTACTTTTAGCTCGTACAAAATACAATATAC 790                 810                 830
TTTTCATTTCTCCGTAAACAACCTGTTTTCCCATGTAATATCCTTTTCTATTTTTCGTTT 850                 870
CGTTACCAACTTTACACATACTTTATATAGCTAT, wherein
```

Nucleotide sequence of the MFα1-HPTH fusion gene from pSSαLX5-HPTH1. Nucleotide nos. 1-173 makeup the MFα1 promoter region and 5' noncoding sequence. 174-440 is the MFα1 N-terminal coding sequence. 441-695 is the HPTH sequence obtained from pSSHPTH-10. 696-726 is an HPTH 3' noncoding sequence from pSSHPTH-10. 727-732 is from pUC19. 733-874 is MFα 3' noncoding sequence and transcriptional termination signal.

```
         10                  30                  50
AGTGCAAGAAAACCAAAAAGCAACAACAGGTTTTGGATAAGTACATATATAAGAGGGCCT 70                  90                 110
TTTGTTCCCATCAAAAATGTTACTGTTCTTACGATTCATTTACGATTCAAGAATAGTTCA 130                 150                 170
AACAAGAAGATTACAAACTATCAATTTCATACACAATATAAACGACCAAAAGAATGAGAT 190                 210                 230
TTCCTTCAATTTTTACTGCAGTTTTATTCGCAGCATCCTCCGCATTAGCTGCTCCAGTCA 250                 270                 290
ACACTACAACAGAAGATGAAACGGCACAAATTCCGGCTGAAGCTGTCATCGGTTACTCAG 310                 330                 350
ATTTAGAAGGGGATTTCGATGTTGCTGTTTTGCCATTTTCCAACAGCACAAATAACGGGT 370                 390                 410
TATTGTTTATAAATACTACTATTGCCAGCATTGCTGCTAAAGAAGAAGGGGTATCTTTGG 430                 450                 470
ATAAAAGAGAGGCTGAAGCTTCTGTGAGTGAAATACAGCTTATGCATAACCTGGGAAAAC 490                 510                 530
ATCTGAACTCGATGGAGAGAGTAGAATGGCTGCGTAAGAAGCTGCAGGATGTGCACAATT 550                 570                 590
TTGTTGCCCTTGGAGCTCCTCTAGCTCCCAGAGATGCTGGTTCCCAGAGGCCCCGAAAAA
```

FIG. II CONT.

```
        610                 630                 650
AGGAAGACAATGTCTTGGTTGAGAGCCATGAAAAAAGTCTTGGAGAGGCAGACAAAGCTG 670                 690                 710
ATGTGAATGTATTAACTAAAGCTAAATCCCAGTGAAAATGAAAACAGATATTGTCAGAGT 730                 750                 770
TCTGCTCTAGAGTCGACTTTGTTCCCACTGTACTTTAGCTCGTACAAAATACAATATAC 790                 810                 830
TTTTCATTTCTCCGTAAACAACCTGTTTTCCCATGTAATATCCTTTTCTATTTTTCGTTT 850                 870
CGTTACCAACTTTACACATACTTTATATAGCTAT
```

AN ELECTROPHORESIS PLATE SHOWING THE HUMAN PARATHYROID HORMONE PRODUCED AND SECRETED BY YEAST AND RECOVERED FROM THE YEAST CULTURE MEDIUM.

PRODUCTION OF HUMAN PARATHYROID HORMONE FROM MICROORGANISMS

This is a continuation, of application Ser. No. 06/921,684 filed Oct. 22, 1986.

FIELD OF THE INVENTION

This invention relates to genetically engineered microorganisms containing DNA coding for human preproparathyroid hormone.

BACKGROUND OF THE INVENTION

A number of proteins and peptides that are normally synthesized by mammalian cells have proven to have medical, agricultural and industrial utility. These proteins and peptides may be of different molecular size and have a number of different functions, for example, they may be enzymes, structural proteins, growth factors and hormones. In essence both proteins and peptides are composed of linear sequences of amino acids which form secondary and tertiary structures that are necessary to convey the biological activity. Human parathyroid hormone has a relatively small molecular weight, which has made it possible to synthesize the peptide chemically by the sequential addition of amino acids. Thus, parathyroid hormone is commercially available, but in very small quantities at high cost. As a result, there is no human parathyroid hormone available at a reasonable price to supply the many potential medical, agricultural and industrial applications.

During the past ten years, microbiological techniques employing recombinant DNA have made it possible to use microorganisms for the production of species-different peptides. The microorganism is capable of rapid and abundant growth and can be made to synthesize the foreign product in the same manner as bacterial peptides. The utility and potential of this molecular biological approach has already been proven by microbiological production of a number of human proteins that are now available for medical and other uses.

Parathyroid hormone (PTH) is one of the most important regulators of calcium metabolism in mammals and is also related to several diseases in humans and animals, e.g. milk fever, acute hypocalsemia and otherwise pathologically altered blood calcium levels. This hormone therefore will be important as a part of diagnostic kits and will also have potential as a therapeutic in human and veterinary medicine.

The first synthesis of DNA for human preproparathyroid hormone was described by Hendy, G. N., Kronenberg, H. M., Potts, Jr. J. T. and Rich, A., 78 Proc. Natl. Acad. Sci. 7365–7369 (1981). DNA complementary in sequence to PTH mRNA was synthesized and made double stranded (Hendy et al., supra). This cDNA was cloned in pBR 322 DNA and *E. coli* 1776 was transfected. Of the colonies with correct antibiotic resistance, 23 out of 200 clones were identified as containing specific human PTH cDNA inserts. However, none of the 23 human PTH clones contained the full length insert (Hendy et al., supra). Later Breyel, E., Morelle, G., Aufmkolk, B., Frank, R., Blocker, H. and Mayer, H., *Third European Congress on Biotechnology*, 10–14 Sept. 1984, Vol. 3, 363–369, described the presence of the human PTH gene in a fetal liver genomic DNA library constructed in the phage Charon 4A. A restriction enzyme fragment of the PTH gene was recloned and transfected into *E. coli*.

However, the work of Breyel et al., supra, demonstrated that *E. coli* degrades human PTH. Thus, a microorganism which shows a stable production of intact human parathyroid hormone has so far not been described. Further, parathyroid hormone has never before been isolated from yeast.

SUMMARY OF THE INVENTION

Accordingly, it is an object of the present invention to provide a plasmid containing DNA coding for human preproparathyroid hormone (HPTH) for insertion in *Escherichia coli*. It is another object of the present invention to provide a genetically engineered *E. coli* containing DNA coding for human preproparathyroid hormone.

A further object of the present invention is to provide a plasmid for insertion in yeast containing DNA coding for parathyroid hormone. It is also an object of the present invention to provide a transformed yeast containing DNA coding for parathyroid hormone, including human parathyroid hormone, and from which transformed yeast, parathyroid hormone may be obtained.

Other objects and advantages of the present invention will become apparent as the description thereof proceeds.

In satisfaction of the foregoing objects and advantages, there is provided by the present invention a novel plasmid for insertion in *E. coli*, containing DNA coding for human preproparathyroid hormone. The plasmid, when inserted into *E. coli*, functions to transform the *E. coli* such that the *E. coli* then produces multiple copies of the plasmid, and thus of the cDNA coding for human preproparathyroid hormone. The plasmid for insertion into *E. coli* of the present invention and thus the transformed *E. coli* are distinguishable over prior art plasmids and microorganisms, for example as described in Hendy et al., supra, in that the plasmid of the present invention contains a double start codon at the 5' end of the DNA coding for preproparathyroid hormone. The presence of the double start codon may cause a production microorganism transformed with a plasmid containing this cDNA to produce preproparathyroid hormone at an increased rate and in an improved yield over prior art transformed microorganisms.

There is further provided by the present invention a plasmid for insertion in yeast containing DNA coding for parathyroid hormone. In a preferred embodiment, this plasmid is prepared by recloning the plasmid for insertion in *E. coli* described above. Finally, the invention provides a yeast transformed by said plasmid for insertion in yeast such that the yeast produces and secretes parathyroid hormone. Thus, the invention provides a method by which parathyroid hormone may be isolated from yeast culture medium. In a preferred embodiment, the transformed yeast is Saccharomyces cerevisiae. In another preferred embodiment, the parathyroid hormone is human parathyroid hormone.

Samples of pSSHPTH-10, *E. coli* transformed therewith, pSSαL×5-HPTH1 and Saccharomyces cerevisiae transformed therewith were deposited in the American Type Culture Collection in Rockville, Md. on Sept. 29, 1986, under the provisions of the Budapest Treaty. The samples have been accorded the following deposit numbers:

Transformed *E. coli* containing pSSHPTH-10: ATCC 67223.

pSSHPTH-10: ATCC 40267.

Transformed *S. cerevisiae* containing pSSαL×5-HPTH1: ATCC 20821.
pSSαL×5-HPTH1: ATCC 40266.

BRIEF DESCRIPTION OF THE DRAWINGS

FIG. 1 shows all possible variations of the DNA sequence coding for human preproparathyroid hormone.

FIG. 2 shows the specific human preproparathyroid hormone DNA coding sequence of the clone pSSHPTH-10.

FIG. 3 shows a DNA sequence coding for human preproparathyroid hormone and having a double start codon at the 5' terminal end with flanking sequences in which are shown all possible variations of the DNA which may be present on the plasmid of the present invention.

FIG. 4 shows the specific human preproparathyroid hormone DNA coding sequence of the clone pSSHPTH-10 with flanking sequences.

FIG. 5 shows the actual amino acids sequence of the human preproparathyroid hormone for which the DNA sequence in clone pSSHPTH-10 codes.

FIG. 9 shows the construction and schematic drawing of pSSαL×5-HPTH1.

FIG. 10 shows the sequence of the MFα1-HPTH fusion gene with all possible combinations of the DNA coding for HPTH.

FIG. 11 shows the sequence of the MFα1-HPTH fusion gene.

DETAILED DESCRIPTION OF THE PREFERRED EMBODIMENTS

Figure 6:
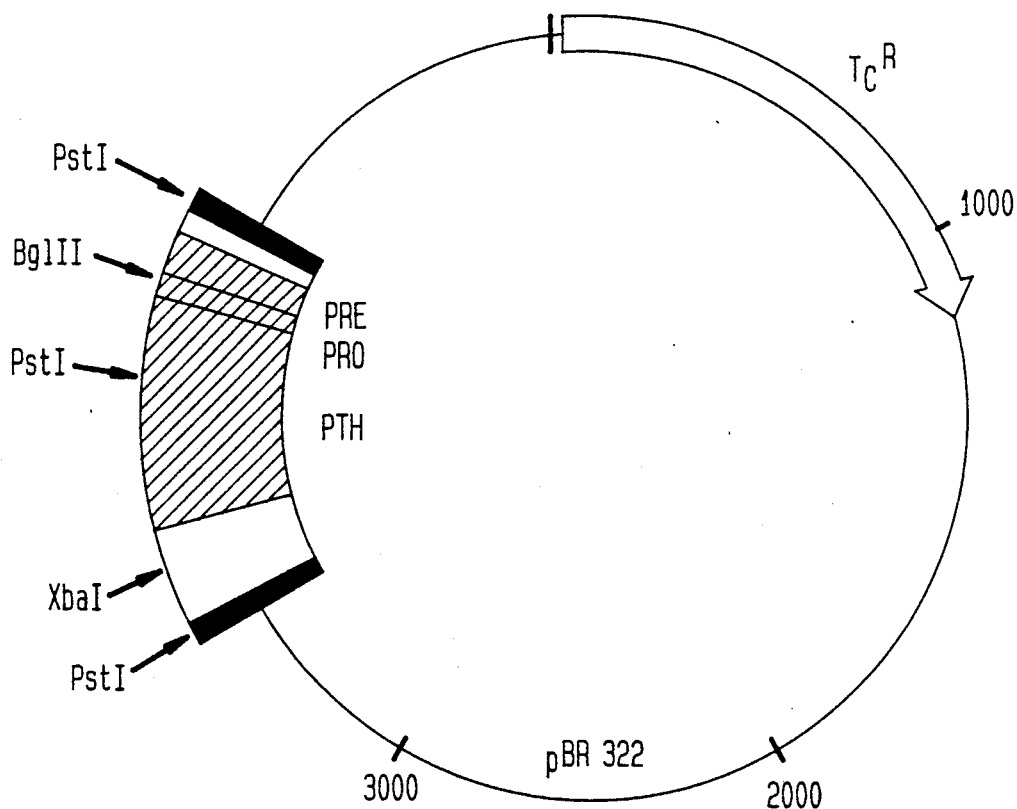
FIG. 6 shows the composition of the recombinant plasmid pSSHPTH-10.

As indicated above, the present invention is directed to a plasmid for insertion in *E. coli* containing DNA coding for human preproparathyroid hormone. The invention is also directed to the resulting transformed *E. coli*.

The invention further is directed to a plasmid for insertion into yeast which contains DNA coding for parathyroid hormone and which is derived from the plasmid for insertion into *E. coli*. Finally, the invention is directed to a transformed yeast from which parathyroid hormone may be recovered.

The invention further provides methods of producing and isolating the plasmids and transformed microorganisms. Poly(A) selected RNA was isolated from human parathyroid adenomas collected immediately after surgery. The poly(A) RNA was enriched for correct size mRNA by ultracentrifugation through sucrose gradients. Preproparathyroid hormone of correct molecular weight was translated in vitro from this size fractionated poly(A) RNA as judged by sodium dodecylsulphate polyacrylamide gel electrophoresis after immuno precipitation with antiparathyroid antiserum. The specific messenger RNA for the human PTH was used as template for complementary DNA synthesis using oligo d(T)18 as a primer and avian myoblastosis virus reverse transcriptase. After removal of the RNA templates by alkali hydrolysis, the second strand complementary DNA was synthesized by incubating the purified first strand DNA in the presence of the Klenow fragment of *E. coli* DNA polymerase I. The double stranded complementary DNA was made blunt ended by the action of *Aspergillus oryzae* single strand specific endonuclease S1 and complementary DNA longer than 500 base pairs was isolated after neutral sucrose gradient centrifugation. Approximately 20 bases long d(C)-tail protrusions were enzymatically added to the 3' ends of the cDNA. This modified complementary DNA was annealed to restriction endonuclease PstI cleaved and d-tailed vector pBR 322. Resulting recombinant plasmid DNA's were transformed into *E. coli* KI2 BJ 5183. Positive transformants were analysed for by colony hybridization using two different synthetic deoxyribo-oligonucleotides which covered the N-terminal coding region as well as the 3' noncoding part of the hormone mRNA sequence, respectively. Six out of 66 clones that were positive for both probes were submitted for detailed analysis by restriction endonuclease mapping showing that they all were identical except for some size heterogenity at the regions flanking the start codon and the XbaI site 3' for the stop codon. One clone, pSSHPTH-10, was subjected to DNA sequence analysis revealing a 432 nucleotide long human parathyroid hormone complementary DNA sequence inserted in the PstI site of pBR 322. The entire cDNA sequence was found to be identical to the sequence previously described by Hendy, et al., supra, except for a five base pair deletion in front of the start codon.

FIG. 2 shows the human preproparathyroid hormone DNA sequence of pSSHPTH-10. This may be compared with FIG. 1, which shows all possible variations of the DNA sequence for human preproparathyroid hormone without the 5' double start codon. FIG. 3 shows the DNA sequence of the clone of the present invention with the flanking sequences. In a preferred embodiment, the plasmid for insertion in *E. coli* coding for human preproparathyroid hormone is pSSHPTH-10, the DNA sequence of which, including the flanking sequence, is shown in FIG 4.

The invention further provides a plasmid for insertion into yeast containing DNA coding for parathyroid hormone. The parathyroid hormone may be human or animal parathyroid hormone, for example pig or bovine parathyroid hormone. The plasmid for insertion in yeast of the present invention may be recloned from plasmids containing DNA coding for human or animal parathyroid hormone. In a preferred embodiment, the plasmid for insertion in yeast contains DNA coding for human parathyroid hormone. As shown in the following examples, the HPTH sequence from pSSHPTH-10 has been recloned and inserted in specially designed vectors for expression in *Saccharomyces cerevisiae*.

pSSHPTH-10 was digested to form a 288 bp BglII-XbaI fragment. This fragment was then subcloned into pUC19 between the BamHI and XbaI sites. The subclone was then digested with Dpn I, and the largest resulting fragment was isolated. The said fragment was then digested with SalI.

The plasmid pSSαL×5-HPTH1 that in yeast MATα cells leads to the expression and secretion of PTH was constructed in three stages:

1. Construction of the yeast shuttle vector pL4 (which replicates in both *E. coli* and *Saccharomyces cerevisiae*).
2. Cloning of a DNA fragment containing the yeast mating pheromone MFα1 gene and its insertion into the yeast shuttle vector to make the paL×5 vector.

3. Insertion of a DNA fragment from the coding region of the HPTH gene of pSSHPTH-10 into paL×5 in reading frame with the prepro part of the MFα1 gene, thereby producing the vector pSSαL×5-HPTH1.

The shuttle vector pL4 was constructed by inserting into pJDB207, an EcoRI-AvaII fragment containing the ADHI promoter isolated from pADH040. A SphI fragment was then deleted, resulting in a plasmid pAL×1. The PstI site in the β-lactamase gene was deleted and the plasmid was partially digested with PvuI and BglI and ligated to a PvuI BglI fragment of pUC8, to form pAL×2. After a further oligonucleotide insertion, the plasmid was digested with HindIII and religated to form pAL×4.

Total yeast DNA from the Y288C strain was digested with EcoRI, and the 1.6-1.8 kb fragments isolated. These were ligated to EcoRI-cleaved pBR322, and *E. coli* was transformed. The clones were screened for MFα1 inserts by oligonucleotide hybridization. The DNA selected thereby was then used to transform *E. coli*. The resulting plasmid pMFα1-1 was digested with EcoRI, made blunt ended by Klenow enzyme, and then digested with BglII. The MFα1 fragment was isolated, and ligated to pL5 (digested with BamHI, made blunt ended with Klenow enzyme, and digested with BglII) to yield paL×5.

In order to insert the human PTH cDNA fragment into paL×5, the paL×5 was digested with HindIII, creating sticky ends and the site was made blunt ended with the DNA polymerase I Klenow fragment and dNTP. The paL×5 was then digested with SalI to create a sticky ended DNA complementary to the SalI digested human PTH fragment described above.

Figure 12:
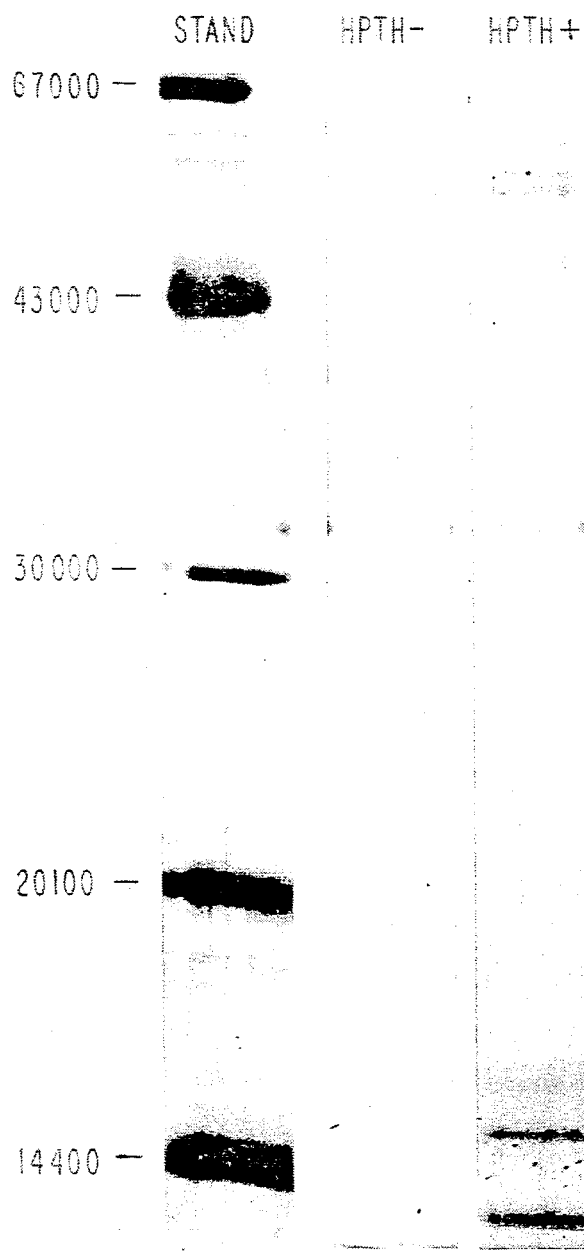
FIG. 12 shows an electrophoresis plate showing the human parathyroid hormone produced and secreted by yeast and recovered from the yeast culture medium.

The SalI digested human PTH fragment was then inserted into the SalI digested paL×5. The resulting plasmid pSSαL×5-PTH is shown in FIG. 9.

pSSαL×5-PTH was then inserted into yeast, thereby transforming yeast so that the yeast produces and secretes human parathyroid hormone. In a preferred embodiment, the transformed yeast is *Sacchromyces cerevisiae*. An electrophoresis plate showing the human parathyroid hormone from the yeast culture medium is shown at FIG. 12.

Although the method for making the plasmid for insertion in yeast by recloning pSSHPTH-10 is shown in detail, this method is shown to illustrate the invention, and the invention is not limited thereto. The method may be applied to a variety of other plasmids containing DNA coding for human or animal PTH to produce the plasmid for insertion in yeast of the present invention.

The plasmids of the present invention and transformed microorganisms were produced as set forth in the following examples.

EXAMPLE I

Isolation of mRNA and synthesis of complementary DNA (cDNA) of human parathyroid hormone Starting material for the invention was parathyroid adenomas obtained from patients by surgery. The parathyroid tissue was placed on dry ice directly after removal and transported to a laboratory for preparation of RNA. The frozen tissue was homogenized with an ultra Turax homogenizer in the presence of 4M Guanidinium thiocyanate and the RNA content was recovered by serial ethanol precipitations as described by Chirgwin, J. M., Przybyla, A. E., MacDonald, R. J. and Rutter, W. J., 18 *Biochemistry* 5294-5299 (1979). The RNA preparation was applied to oligo d(T) cellulose affinity chromatography column in order to enrich for poly(A) containing mRNA. The poly(A) rich RNA was further enriched for parathyroid hormone (PTH) mRNA sized RNA by ultracentrifugation through a 15-30% linear sucrose gradient. The resulting gradient was divided into 25 fractions and every third fraction was assayed for PTH mRNA content by in vitro translation followed by immunoprecipitation with anti PTH antiserum (Gautvik, K. M., Gautvik, V. T. and Halvorsen, J. F., *Scand. J. Clin. Lab. Invest.* 43, 553-564 (1983)) and SDS-polyacrylamide gel electrophoresis (Laemmeli, U. K., 227 *Nature* 680 (1970)). The RNA from the fractions containing translatable PTH mRNA was recovered by ethanol precipitation. This RNA, enriched for PTH mRNA, was used as a template for cDNA synthesis using oligo d(T)18 as a primer and avian myoblastosis virus reverse transcriptase for catalysis of the reaction (Maniatis, T., Fritsch, E. F. and Sambrook, J., *Molecular Cloning pp.* 230-243 (1982)). After first strand synthesis, the RNA templates were removed by alkali hydrolysis. The second strand cDNA was synthesized by incubating the purified first strand cDNA in the presence of the Klenow fragment of *E. coli* DNA polymerase I (Maniatis, supra). This in vitro synthesized double stranded cDNA was made blunt ended by the action of *Aspergillus oryzae* single strand specific endonuclease S1 (Maniatis, supra). The blunt ended double stranded cDNA was size fractionated over a 15-30% neutral sucrose gradient. The size distribution of each fraction was estimated by agarose gel electrophoresis together with known DNA fragment markers. Fractions containing cDNA larger than approximately 500 base pairs were pooled and the cDNA content was collected by ethanol precipitation.

EXAMPLE 2

Cloning of cDNA P1H in plasmid pBR 322 and transformation of *E. coli* K12 BJ5183

An approximate 20 base long d(C)-tail protrusion was enzymatically added to the 3' ends of the cDNA by the action of terminal deoxynucleotidyl transferase (Maniatis, supra). The C-tailed cDNA was annealed to restriction endonuclease PstI cleaved and G-tailed vector pBR322 and the resulting recombinant plasmid DNA's were transformed into *E. coli* K12 BJ 5183 cells which were made competent by the method of Hanahan, D., 166 *J. Mol. Biol.* 557-580 (1983). A total of 33,000 transformants were analyzed for PTH cDNA content by colony hybridization (Hanahan, D. and Meselson, 10 *Gene* 63 (1980)).

Two to three thousand transformants were plated directly on each 82 mm diameter nitrocellulose filter, placed on top of rich medium agar plates containing tetracycline, and incubated at 37 degrees Centigrade until approximately 0.1 mm diameter colonies appeared. Duplicate replicas of each filter was obtained by serial pressing of two new filters against the original filter. The replica filters were placed on top of new tetracycline containing agar plates and incubated at 37 degrees Centigrade until approximately 0.5 mm diameter colonies appeared. The master filter with bacterial colonies was kept at 4 degrees Centigrade placed on top of the agar plate and the duplicate replica filters were removed from the agar plates and submitted to the following colony hybridization procedure.

EXAMPLE 3

Characterization of bacterial clones containing recombinant PTH cDNA and of the DNA sequence of clone pSSHPTH-10

The cells in the respective colonies were disrupted in situ with alkali and sodium chloride leaving the DNA content of each bacterial clone exposed. The procedure allows the DNA to bind to the filter after which it was neutralized with Tris-buffer and dried at 80 degrees Centigrade. The majority of cell debris was removed by a 65 degree Centigrade wash with the detergent sodium dodecylsulphate (SDS) and sodium chloride leaving the DNA bound to the filters at the position of the former bacterial colonies. The filters were presoaked in 6×SSC (0.9M NaCl, 0.09M Na-citrate), 1× Denhart's solution (0.1 g/ml Ficoll, 0.1 g/ml polyvinyl pyrrolidone, 0.1 g/ml bovine serum albumin), 100 g/ml herring sperm DNA, 0.5% SDS and 0.05% sodium pyrophosphate for two hours at 37 degrees Centigrade (Woods, D. E., 6 Focus No. 3. (1984)).

The hybridization was carried out at 42 degrees Centigrade for 18 hours in a hybridization solution (6× SSC, 1× Denhart's solution, 20 g/ml tRNA and 0.05% sodium pyrophosphate) supplemented with 32P-labelled DNA probe (Woods, supra).

The DNA used as a hybridization probe was one of two different synthetic deoxyribo oligonucleotides of which the sequences were deduced from the published human PTH cDNA sequence of Hendy, et al., supra. The first probe was a 24-mer oligonucleotide originating from the start codon region of the human pre-proPTH coding sequence having a nucleotide sequence reading TACTATGGACGTTTTCTGTACCGA. The second oligonucleotide was a 24-mer spanning over a cleavage site for the restriction endonuclease XbaI located 31 nucleotides downstream of the termination codon and consisted of the nucleotide sequence CTCAAGACGAGATCTGTCACATCC.

Labelling was carried out by transfer of 32 P from 32 P-γ-ATP to the 5' end of the oligonucleotides by the action of polynucleotide kinase (Maxam, A. M. and Gilbert, W., 65 Methods Enzymol., 499 (1980)).

The hybridized filters were washed in 6×SSC, 0.05% sodium pyrophosphate at 42 degrees Centigrade prior to autoradiography. Sixty-six clones were found to be positive for both probes as judged from hybridization to both copies of the duplicate replica filters. All those were picked from the original filters with the stored cDNA library and amplified for indefinitive storage at −70 degrees Centigrade. Six of these were chosen for plasmid preparation and a more detailed analysis by restriction endonuclease mapping, showing that all were identical except for some size heterogenity at the regions flanking the start codon and XbaI site, respectively.

EXAMPLE 4

Clone pSSHPTH-10

One clone, pSSHPTH-10, was subjected to DNA sequence analysis according to the method of Maxam and Gilbert, supra. The complete structure of pSSHPTH-10 is shown in FIG. 6. This clone consists of a 432 base pair long PTH cDNA sequence inserted in the PstI site of pBR322 having 27 G/C base pairs at the 5' end and 17 G/C base pairs at the 3' end. The complete DNA sequence of the cDNA insert of pSSHPTH-10 is shown in FIG. 4. It is identical to the sequence of Hendy, et al., supra, except for a five base pair deletion right in front of the start codon, changing the published (Hendy, et al., supra) start-stop (ATGTGAAG) signal (deletion is underlined) preceding the used start codon (ATG) to a double start signal (ATGATG).

EXAMPLE 5

Construction of the yeast shuttle vector pL4

Before the HPTH-yeast-expression project was initiated, a family of general yeast expression vectors were developed. One of these, pL4, later was used to make pSS αL×5-HPTH1, as described below:

The plasmid pJDB207, constructed by Beggs, J. D., "Multiple-copy yeast plasmid vectors," Von Wettstein, D., Friis, J., Kielland-Brandt, M. and Stenderup, A. (Eds) Molecular Genetics in Yeast (1981), Alfred Benzon Symposium Vol. 16, 383–390, was chosen as the basis for the general expression vectors. It contains an EcoRI fragment of the yeast 2 micron DNA inserted into the pBR322 derivative pAT153. It also contains the yeast LEU2 gene. The copy number of pJDB207 in yeast cir+ cells is very high relative to that of other plasmids and it is unusually stable after non-selective growth in a cir+ strain. Parent, S. A., Fenimore, C. M., and Bostian, K. A. "Vector Systems for the Expression, Analysis and Cloning of DNA Sequences in S. cerevisiae," 1 Yeast 83–138 (1985); Erhart, E. and Hollenberg, C. P., "The Presence of a Defective LEU2 Gene on 2 Micron DNA Recombinant Plasmids of Saccharomyces cerevisiae is Responsible for Curing and High Copy Number," 156 J. Bacteriol 625–635 (1983). These properties are related to a partial defective promoter in the selective marker gene LEU2 (often named LEU2d, d for defective), Erhart et al., supra, which is not changed in the following constructs.

A 1260 base pair EcoRI-AvaII fragment containing the ADHI promoter was isolated from the plasmid pADH040. After a fill in reaction with the Klenow fragment of DNA polymerase I and all four dNTPs, BamHI linkers were attached and the fragment was cloned into the unique BamHI site of pJDB207. From the plasmid with the promoter in a counterclockwise direction, a 1050 base pair SphI fragment was then deleted (from the SphI site in pJDB207 to the SphI site in the promoter fragment) leaving only a single BamHI site. This plasmid was designated pALX1.

The PstI site in the β-lactamase gene of pALX1 then was eliminated without inactivating the gene. pALX1 was digested to completion with PstI and nuclease S1 to destroy the PstI site, and then subjected to a partial digestion with PvuI and BglI. At the same time, a 250 base pair PvuI BglI fragment was isolated from pUC8, Vieira, J. and Messing, J., 19 Gene 259 (1982), that contains the corresponding part of a β-lactamase gene without a PstI site. This was ligated to the partially digested pALX1. In all the ampicillin resistant clones isolated the β-lactamase gene had been restored by incorporating the pUC8 fragment. This plasmid was called pALX2.

The following oligonucleotide was purchased from Prof. K. Kleppe, University of Bergen, and inserted into the BamHI site of pALX2:

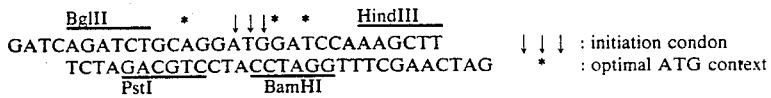

```
      BglIII        *   ↓↓↓*  *   HindIII
    GATCAGATCTGCAGGATGGATCCAAAGCTT       ↓↓↓ : initiation condon
        TCTAGACGTCCTACCTAGGTTTCGAACTAG    *   : optimal ATG context
            PstI          BamHI
```

Plasmids with the proper orientation were isolated and designated pALx3.

Figure 7:
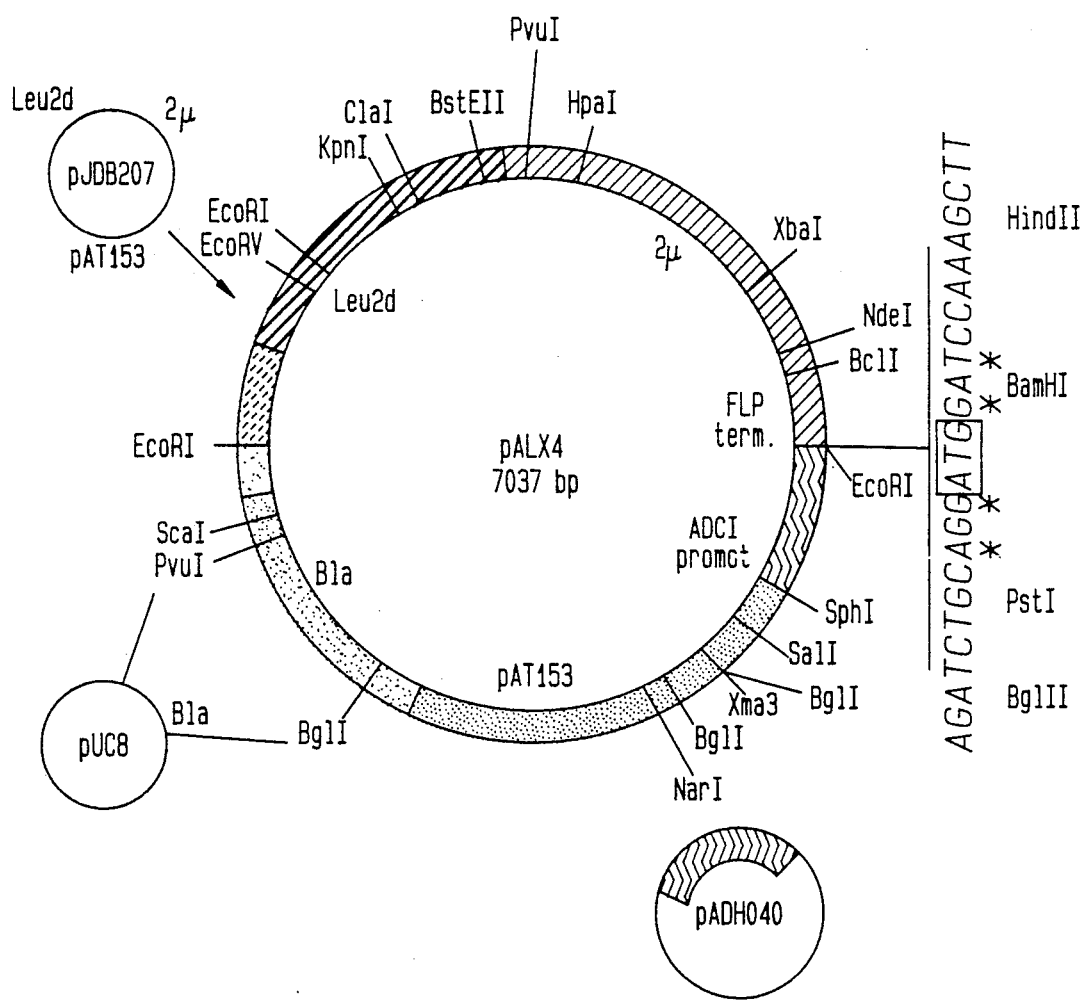
FIG. 7 shows a map of pAL×4.

Finally the pALx3 was digested with HindIII and religated to delete a HindIII fragment of 480 base pairs. The resulting vector is called pALx4. A map of pALx4 is shown in FIG. 7.

pL4 is a derivative of pALx4 in which the ADHI promoter is deleted. pL4 was used as basis for the insertion of other promoters. pALx4 was first digested with BglII and SalI. The resulting sticky ends were filled in with the Klenow fragment of DNA polymerase I and 4 dNTPs, followed by religation. By this treatment, the ADHI promoter is eliminated and the BglII site regenerated to give the vector pL4.

EXAMPLE 6

Construction of paLx5

The gene for the yeast mating pheromone MF 1 was first cloned by Kurjan, J. and Herskowitz, I., "Structure of a Yeast Pheromone Gene (MF): A Putative α-Factor Precursor Contains Four Tandem Copies of Mature α-Factor", 30 Cell, 933–943 (1982). The published sequence was used to reclone the MF 1 gene. Total yeast DNA from the strain Y288C was digested with EcoRI and digestion products in the size range from 1.6 to 1.8 kb were isolated from a preparative agarose gel. These were then ligated to dephosphorylated EcoRI cleaved pBR322 and used to transform E. coli BJ5183. The resulting clones were screened for MFα1 gene inserts by hybridization to a labeled oligonucleotide of the following composition:

TGGCATTGGCTGCAACTAAAGC

Figure 8:
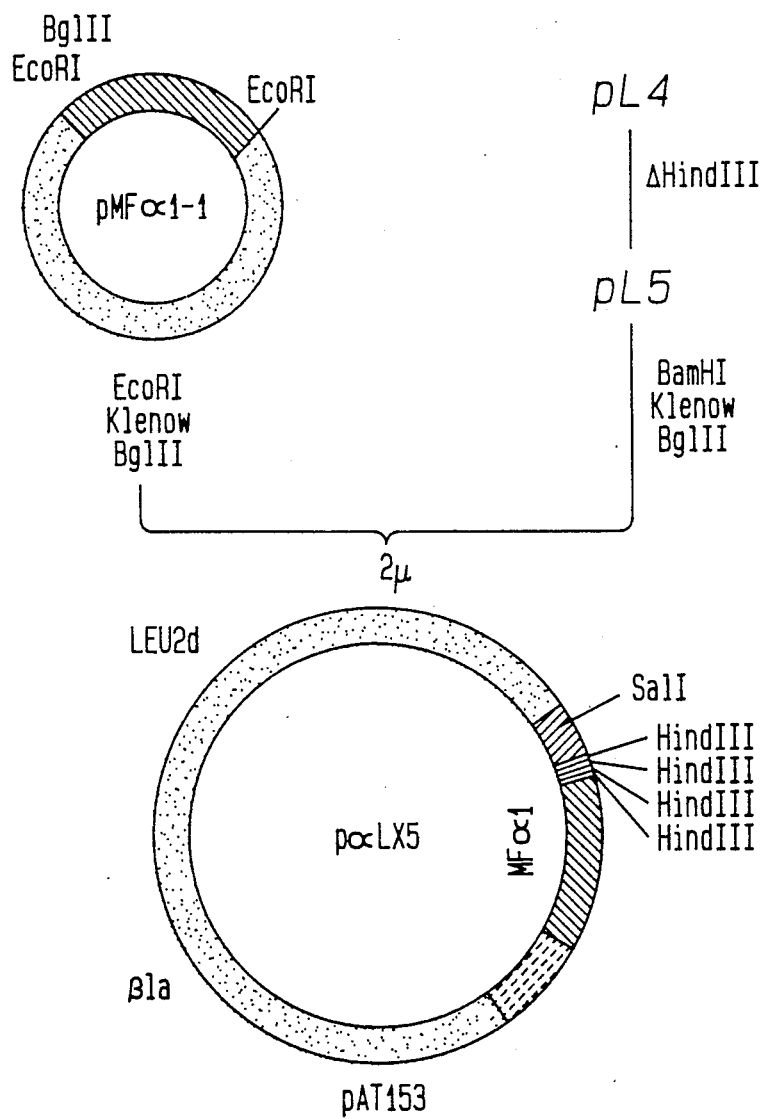
FIG. 8 shows the construction of pαL×5 from pL4 and pMFα1-1.

DNA from purified positive clones was then used to transform E. coli JA221 from which plasmid DNA was prepared. The plasmid used in the following constructs, pMFα1-1, is shown in FIG. 8.

pMFα1-1 was digested with EcoRI, filled in with the Klenow fragment of DNA polymerase I and 4 dNTPs, phenol extracted and digested with BglII. The 1.7 kb MFα1 gene fragment was isolated from an agarose gel. Before inserting it into the yeast shuttle vector, the HindIII site of pL4 was eliminated by HindIII digestion, Klenow fill-in reaction and religation to give the pL5 shuttle vector. pL5 was digested with BamHI, filled in with the Klenow fragment of DNA polymerase I and 4 dNTPs, phenol extracted and digested with BglII. After purification on gel it was ligated to the MFα1 fragment to give the expression vector paLx5 as shown in FIG. 8.

EXAMPLE 7

Construction of pSSαLx5-HPTH1

A 288 base pair BglII XbaI fragment from the pSSHPTH-10 plasmid was isolated and subcloned in pUC19 using the BamHI and XbaI site of this vector. This subclone designated pUC-HPTH, was digested with DpnI and the largest fragment isolated. This fragment was then digested with SalI and the smallest of the two resulting fragments was again isolated, yielding a sticky end on the SalI cut side and a blunt end at the DpnI cut side.

αLx5 was digested with HindIII, filled in with the Klenow fragment of DNA polymerase I and 4 dNTPs, phenol extracted and digested with SalI. After purication from gel, it was ligated to the HPTH fragment described above. The resulting clones had the HindIII site regenerated verifying that the reading frame was correct. This plasmid called pSSα1-HPTH1 is shown in FIG. 9. The sequence of the MFα1-HPTH fusion gene is shown in FIG. 10.

EXAMPLE 8

Expression And Secretion Of HPTH In Yeast

The yeast strain FL200 (α, ura3, leu2) was transformed with the plasmids paLx5 and pSSαLx5-HPTH1 using the spheroplast method. One transformant of each kind was grown up in leu⁻ medium and aliquots of the cell-free medium were analysed by SDS-PAGE developed by silver-staining (FIG. 12). Two major bands were seen in the medium from the pSSαLx5-HPTH1 transformant that were not present in the medium from the paLx5 transformant: one band of approximately 9000 daltons, the expected size of HPTH, and one band of approximately 16000 daltons that could correspond to an unprocessed MFα1-HPTH fusion product. Both polypeptides reacted with antibodies against human PTH in a manner identical to the native hormone.

The examples are included by way of illustration, but the invention is not limited thereto. While the above examples are directed to providing a S. cerevisiae which produces and excretes human parathyroid hormone, the method of the present invention may be applied to produce a plasmid containing DNA coding for parathyroid hormone from any species. Further, said plasmid may be inserted into any species of yeast. The invention thus is not limited to S. cerevisiae.

The cloned human parathyroid hormone produced by the yeast of the present invention has a variety of known and potential uses. For example, it is current medical theory that human parathyroid hormone will be highly effective in treating osteoporosis. Genetically engineered parathyroid hormone may be useful in an analytical kit for measuring parathyroid hormone levels in humans and animals. Human parathyroid hormone or fragments thereof may also be used for treatment of humans or animals displaying reduced or pathologically altered blood calcium levels. It is anticipated that many other uses will be discovered when genetically engineered parathyroid hormone is available in large quantities, for example as a result of the present invention.

The invention has been described herein with reference to certain preferred embodiments. However, as obvious variations thereon will become apparent to those skilled in the art, the invention is not to be considered limited thereto.

We claim:

1. A DNA sequence encoding Saccharomyces mating factor alpha 1 operably linked to human parathyroid hormone wherein said DNA sequence can stably transform a yeast cell to express and secrete an intact human parathyroid hormone.

2. The DNA sequence of claim 1 wherein said DNA sequence comprises the nucleotide sequence set forth in FIG. 11.

3. The yeast cell of claim 1 wherein said cell is in the genus Saccharomyces.

4. The yeast cell of claim 1 wherein said cell is of the species *Saccharomyces cerevisiae.*

5. The yeast cell of claim 1 wherein said cell is a budding yeast cell.

6. The human parathyroid hormone of claim 1 wherein said hormone has biological activity substantially equivalent to naturally occurring human parathyroid hormone.

7. A plasmid comprising the DNA sequence of claim 1.

8. A plasmid according to claim 7 wherein said nucleotide sequence comprises:

```
                10                      30                      50
ATGATGATHCCNGCNAARGAYATGGCNAARGTNATGATHGTNATGYTNGCNATHTGYT 70                      90                     110
YTNACNAARWSNGAYGGNAARWSNGTNAARAARMGNWSNGTNWSNGARATHCARYTNATG 130                     150                     170
CAYAAYYTNGGNAARCAYYTNAAYWSNATGGARMGNGTNGARTGGYTNMGNAARAARYTN 190                     210                     230
CARGAYGTNCAYAAYTTYGTNGCNYTNGGNGCNCCNYTNGCNCCNMGNGAYGCNGGNWSN 250                     270                     290
CARMGNCCNMGNAARAARGARGAYAAYGTNYTNGTNGARWSNCAYGARAARWSNYTNGGN 310                     330
GARGCNGAYAARGCNGAYGTNAAYGTNYTNACNAARGCNAARWSNCARTRR, wherein
```

M = A or C
R = A or G
W = A or T
S = C or G
Y = C or T
H = A or C or T
N = A or G or C or T.

9. A plasmid according to claim 7 wherein the nucleotide sequence comprises:

```
                10                      30                      50
TATGATGATHCCNGCNAARGAYATGGCNAARGTNATGATHGTNATGYTNGCNATHTGYTT 70                      90                     110
YYTNACNAARWSNGAYGGNAARWSNGTNAARAARMGNESNGTNWSNGARATHCARYTNAT 130                     150                     170
GCAYAAYYTNGGNAARCAYYTNAAYWSNATGGARMGNGTNGARTGGYTNMGNAARAARYT 190                     210                     230
NCARGAYGTNCAYAAYTTYGTNGCNYTNGGNGCNCCNYTNGCNCCNMGNGAYGCNGGNWS 250                     270                     290
NCARMGNCCNMGNAARAARGARGAYAAYGTNYTNGTNGARWSNCAYGARAARWSNYTNGG 310                     330                     350
NGARGCNGAYAARGCNGAYGTNAAYGTNYTNACNAARGCNAARWSNCARTRRAAATGAAA 370                     390                     410
ACAGATATTGTCAGAGTTCTGCTCTAGACAGTGTAGGGCAACAATACATGCTGCTAATTC

430
AAAGCTCTATTA, wherein
```

M = A or C
R = A or G
W = A or T
S = C or T
Y = C or T
H = A or C or T
N = A or G or C or T.

10. A plasmid according to claim 7 wherein the nucleotide sequence comprises:

```
                10                      30                      50
ATGATGATACCTGCAAAAGACATGGCTAAAGTTATGATTGTCATGTTGGCAATTTGTTTT 70                      90                     110
CTTACAAAATCGGATGGGAAATCTGTTAAGAAGAGATCTGTGAGTGAAATACAGCTTATG
```

-continued

```
                130                      150                       170
CATAACCTGGGAAAACATCTGAACTCGATGGAGAGAGTAGAATGGCTGCGTAAGAAGCTG 190                      210                       230
CAGGATGTGCACAATTTTGTTGCCCTTGGAGCTCCTCTAGCTCCCAGAGATGCTGGTTCC 250                      270                       290
CAGAGGCCCCGAAAAAAGGAAGACAATGTCTTGGTTGAGAGCCATGAAAAAAGTCTTGGA 310                      330
GAGGCAGACAAAGCTGATGTGAATGTATTAACTAAAGCTAAATCCCAGTGA.
```

11. A plasmid according to claim 7 wherein the nucleotide sequence comprises:

```
                10                       30                        50
TATGATGATACCTGCAAAAGACATGGCTAAAGTTATGATTGTCATGTTGGCAATTTGTTT 70                       90                        110
TCTTACAAAATCGGATGGGAAATCTGTTAAGAAGAGATCTGTGAGTGAAATACAGCTTAT 130                      150                       170
GCATAACCTGGGAAAACATCTGAACTCGATGGAGAGAGTAGAATGGCTGCGTAAGAAGCT 190                      210                       230
GCAGGATGTGCACAATTTTGTTGCCCTTGGAGCTCCTCTAGCTCCCAGAGATGCTGGTTC 250                      270                       290
CCAGAGGCCCCGAAAAAAGGAAGACAATGTCTTGGTTGAGAGCCATGAAAAAAGTCTTGG 310                      330                       350
AGAGGCAGACAAAGCTGATGTGAATGTATTAACTAAAGCTAAATCCCAGTGAAAATGAAA 370                      390                       410
ACAGATATTGTCAGAGTTCTGCTCTAGACAGTGTAGGGCAACAATACATGCTGCTAATTC

430
AAAGCTCTATTA.
```

12. A microorganism containing the plasmid of claim 8.

13. A microorganism according to claim 12 wherein said microorganism is *Escherichia coli*.

14. A microorganism containing the plasmid of claim 9.

15. A microorganism according to claim 14 wherein the microorganism is *Escherichia coli*.

16. A microorganism containing the plasmid of claim 10.

17. A microorganism according to claim 16 wherein the microorganism is *Escherichia coli*.

18. A microorganism containing the plasmid of claim 11.

19. A microorganism according to claim 18 wherein the microorganism is *Escherichia coli*.

20. A plasmid according to claim 7, wherein the nucleotide sequence comprises:

```
                10                       30                        50
AGTGCAAGAAAACCAAAAAGCAACAACAGGTTTTGGATAAGTACATATATAAGAGGGCCT 70                       90                        110
TTTGTTCCCATCAAAAATGTTACTGTTCTTACGATTCATTTACGATTCAAGAATAGTTCA 130                      150                       170
AACAAGAAGATTACAAACTATCAATTTCATACACAATATAAACGACCAAAAGAATGAGAT 190                      210                       230
TTCCTTCAATTTTTACTGCAGTTTTATTCGCAGCATCCTCCGCATTAGCTGCTCCAGTCA 250                      270                       290
ACACTACAACAGAAGATGAAACGGCACAAATTCCGGCTGAAGCTGTCATCGGTTACTCAG 310                      330                       350
ATTTAGAAGGGGATTTCGATGTTGCTGTTTTGCCATTTTCCAACAGCACAAATAACGGGT 370                      390                       410
TATTGTTTATAAATACTACTATTGCCAGCATTGCTGCTAAAGAAGAAGGGGTATCTTTGG 430                      450                       470
ATAAAAGAGAGGCTGAAGCTWSNGTNWSNGARATHCARYTNATGCAYAAYYTNGGNAARC 490                      510                       530
AYYTNAAYWSNATGGARMGNGTNGARTGGYTNMGNAARAARYTNCARGAYGTNCAYAAYT 550                      570                       590
TYGTNGCNYTNGGNGCNCCNYTNGCNCCNMGNGAYGCNGGNWSNCARMGNCCNMGNAARA
```

-continued

```
         610                    630                        650
ARGARGAYAAYGTNYTNGTNGARWSNCAYGARAARWSNYTNGGNGARGCNGAYAARGCNG 670                    690                        710
AYGTNAAYGTNYTNACNAARGCNAARWSNCARTRRAAATGAAAACAGATATTGTCAGAGT 730                    750                        770
TCTGCTCTAGAGTCGACTTTGTTCCCACTGTACTTTTAGCTCGTACAAAATACAATATAC 790                    810                        830
TTTTCATTTCTCCGTAAACAACCTGTTTTCCCATGTAATATCCTTTTCTATTTTTCGTTT 850                    870
CGTTACCAACTTACACATACTTTATATAGCTAT, wherein
```

M = A or C
R = A or G
W = A or T
S = C or G
Y = C or T
H = A or C or T
N = A or G or C or T.

21. The plasmid of claim 7, wherein the nucleotide sequence comprises:

```
         10                      30                         50
AGTGCAAGAAAACCAAAAAGCAACAACAGGTTTTGGATAAGTACATATATAAGAGGGCCT 70                      90                        110
TTTGTTCCCATCAAAAATGTTACTGTTCTTACGATTCATTTACGATTCAAGAATAGTTCA 130                     150                        170
AACAAGAAGATTACAAACTATCAATTTCATACACAATATAAACGACCAAAAGAATGAGAT 190                     210                        230
TTCCTTCAATTTTTACTGCAGTTTTATTCGCAGCATCCTCCGCATTAGCTGCTCCAGTCA 250                     270                        290
ACACTACAACAGAAGATGAAACGGCACAAATTCCGGCTGAAGCTGTCATCGGTTACTCAG 310                     330                        350
ATTTAGAAGGGGATTTCGATGTTGCTGTTTTGCCATTTTCCAACAGCACAAATAACGGGT 370                     390                        410
TATTGTTTATAAATACTACTATTGCCAGCATTGCTGCTAAAGAAGAAGGGGTATCTTTGG 430                     450                        470
ATAAAAGAGAGGCTGAAGCTTCTGTGAGTGAAATACAGCTTATGCATAACCTGGGAAAAC 490                     510                        530
ATCTGAACTCGATGGAGAGAGTAGAATGGCTGCGTAAGAAGCTGCAGGATGTGCACAATT 550                     570                        590
TTGTTGCCCTTGGAGCTCCTCTAGCTCCCAGAGATGCTGGTTCCCAGAGGCCCCGAAAAA 610                     630                        650
AGGAAGACAATGTCTTGGTTGAGAGCCATGAAAAAAGTCTTGGAGAGGCAGACAAAGCTG 670                     690                        710
ATGTGAATGTATTAACTAAAGCTAAATCCCAGTGAAAATGAAAACAGATATTGTCAGAGT 730                     750                        770
TCTGCTCTAGAGTCGACTTTGTTCCCACTGTACTTTTAGCTCGTACAAAATACAATATAC 790                     810                        830
TTTTCATTTCTCCGTAAACAACCTGTTTTCCCATGTAATATCCTTTTCTATTTTTCGTTT 850                     870
CGTTACCAACTTTACACATACTTTATATAGCTAT.
```

22. A microorganism containing the plasmid of claim 7.

23. A transformed yeast cell comprising a DNA sequence encoding Saccharomyces mating factor alpha 1 operably linked to human parathyroid hormone, said cell capable of expressing said DNA and secreting said expressed DNA into an extracellular environment, whereby said secreted, expressed DNA is intact human parathyroid hormone.

24. The transformed yeast cell of claim 23 wherein said DNA sequence comprises the nucleotide sequence of FIG. 11.

25. The transformed yeast cell of claim 23 wherein said yeast cell is of the genus Saccharomyces.

26. The transformed yeast cell of claim 23 wherein said yeast cell is of the species *Saccharomyces cerevisiae*.

27. The transformed yeast cell of claim 23 wherein said yeast cell is a budding yeast cell.

28. The transformed cell of claim 23 wherein said expressed human parathyroid hormone has a biological activity substantially equivalent to naturally occurring human parathyroid hormone.

29. A DNA sequence comprising a vector capable of stably transforming yeast wherein said DNA sequence encodes Saccharomyces mating factor alpha 1 operably linked to human parathyroid hormone wherein said vector can stably transform a yeast cell to express and secrete an intact human parathyroid hormone.

30. The transformed yeast cell of claim 29 wherein said yeast cell is a budding yeast.

31. The vector of claim 30 wherein said vector is an autonomous replicating plasmid.

32. The vector of claim 30 wherein said vector is an integrating plasmid.

33. The transformed yeast of claim 30 wherein said yeast is from the genus Saccharomyces.

34. The transformed yeast of claim 30 wherein said yeast is of the species *Saccharomyces cerevisiae*.

35. A plasmid, pSSHPTH-10, deposited in the American Type Culture Collection under ATCC No. 40267.

36. A transformed *E. coli* containing pSSHPTH-10, deposited in the American Type Culture Collection under ATCC No. 67223.

37. A transformed *S. cerevisiae* containing pSSαL×5-HPTH1, deposited in the American Type Culture Collection under ATCC No. 20821.

38. A plasmid, pSSαL×5-HPTH1, deposited in the American Type Culture Collection under ATCC No. 40266.

* * * * *

UNITED STATES PATENT AND TRADEMARK OFFICE
CERTIFICATE OF CORRECTION

PATENT NO. : 5,010,010

DATED : April 23, 1991

INVENTOR(S) : Gautvik et al.

It is certified that error appears in the above-identified patent and that said Letters Patent is hereby corrected as shown below:

Column 3, line 59, "in vitro" should read --*in vitro*--.
Column 4, line 10, "d-tailed" should read --d(G)-tailed--; line
Column 5, line 7, that portion of the formula reading "5 -HPTH1" should read --5-HPTH1--
Column 6, line 11, "in vitro" should read --*in vitro*--; line 28, "in vitro" should read --*in vitro*--; line 48, "G-tailed" should read --d(G)-tailed--.
Column 10, line 9, "αLx5" should read --pαLX5--; line 15, "pSSα1-HPTH1" should read --pSSαLX5-HPTH1--; line 66, "Saccharomyces" should read --*Saccharomyces*--.
Column 11, line 7, "Saccharomyces" should read --*Saccharomyces*--.
Column 12, at claim 9, position 98, "E" should read --W--. (See FIG. 3)
Column 15, line 65, "Saccharomyces" should read --*Saccharomyces*--.
Column 16, line 66, "Saccharomyces" should read --*Saccharomyces*--.
Column 17, line 10, "Saccharomyces" should read --*Saccharomyces*--.
Column 18, line 4, "Saccharomyces" should read --*Saccharomyces*--.

In each of the following occurrences, delete multiplication sign and insert --X-- (upper case letter).

Column 2, line 59.
Column 3, line 1; line 2; line 25; line 26; line 29.
Column 4, line 61.

UNITED STATES PATENT AND TRADEMARK OFFICE
CERTIFICATE OF CORRECTION

PATENT NO. : 5,010,010  
DATED : April 23, 1991  
INVENTOR(S) : Gautvik et al.

Page 2 of 2

It is certified that error appears in the above-identified patent and that said Letters Patent is hereby corrected as shown below:

```
Column 5,   line 1; line 5; line 7; line 12; line 15; line 17;
            line 29; line 31, two occurrences; line 34; line 38;
            line 39; line 40.
Column 7,   line 19, two occurrences; line 26; line 27.
Column 8,   line 17; line 52; line 62; line 65; line 68.
Column 9,   line 8; line 9; line 11; line 12; line 13; line 15;
            line 24; line 56; line 61.
Column 10,  line 9; line 23, two occurrences; line 29; line 30.
Column 18,  line 12; line 15.
```

Signed and Sealed this

Twelfth Day of January, 1993

Attest:

DOUGLAS B. COMER

Attesting Officer

Acting Commissioner of Patents and Trademarks